(12) United States Patent
Timperley et al.

(10) Patent No.: US 7,789,884 B2
(45) Date of Patent: Sep. 7, 2010

(54) ACETABULAR RIM CUTTER

(75) Inventors: Andrew John Timperley, St. Leonard's Exeter (GB); Philippe Lavieille, Caen (FR); Pascal Collet, Saint-Martin-De-Fontenay (FR); Franck Le Bon, Evrecy (FR); Robin Sydney Mackwood Ling, Devon (GB); Graham Allan Gie, Devon (GB)

(73) Assignee: Benoist Girard SAS (FR)

( * ) Notice: Subject to any disclaimer, the term of this patent is extended or adjusted under 35 U.S.C. 154(b) by 704 days.

(21) Appl. No.: 11/199,907

(22) Filed: Aug. 9, 2005

(65) Prior Publication Data
US 2006/0079906 A1 Apr. 13, 2006

(30) Foreign Application Priority Data
Oct. 12, 2004 (GB) ................... 0422665.0

(51) Int. Cl.
*A61B 17/16* (2006.01)
(52) U.S. Cl. ............... 606/81; 606/79; 606/80
(58) Field of Classification Search ........... 606/80, 606/81, 86 R, 180, 79; 623/22.21, 22.22, 623/22.23, 22.24, 22.25, 22.26, 22.27, 22.28, 623/22.29, 22.3, 22.31, 22.32, 22.33, 22.34, 623/22.35, 22.36, 22.37, 22.38, 22.39, 22.4, 623/22.41, 22.42, 22.43, 22.44, 22.45, 22.46, 623/23.11, 23.12, 23.13; 408/202, 80
See application file for complete search history.

(56) References Cited

U.S. PATENT DOCUMENTS

| | | | | |
|---|---|---|---|---|
| 3,550,229 A | * | 12/1970 | Zenses | 407/29.13 |
| 4,273,117 A | | 6/1981 | Neuhauser | |
| 4,579,486 A | * | 4/1986 | Damico | 408/204 |
| 4,662,891 A | * | 5/1987 | Noiles | 623/22.31 |
| 4,712,951 A | * | 12/1987 | Brown | 408/158 |
| 5,217,499 A | | 6/1993 | Shelley | |
| 5,462,548 A | * | 10/1995 | Pappas et al. | 606/80 |
| 5,817,096 A | * | 10/1998 | Salyer | 606/81 |
| 5,976,148 A | * | 11/1999 | Charpenet et al. | 606/91 |
| 6,283,971 B1 | * | 9/2001 | Temeles | 606/81 |
| 6,305,885 B1 | * | 10/2001 | Linthicum | 408/1 R |
| 6,918,914 B2 | * | 7/2005 | Bauer | 606/81 |
| 2002/0099380 A1 | * | 7/2002 | Salyer et al. | 606/80 |

(Continued)

FOREIGN PATENT DOCUMENTS

DE 28 30 566 1/1980

(Continued)

OTHER PUBLICATIONS http://dictionary.reference.com, printshot of the definition of "planar" accessed, Dec. 2, 2009.*

*Primary Examiner*—Eduardo C Robert
*Assistant Examiner*—Jan Christopher Merene
(74) *Attorney, Agent, or Firm*—Lerner, David, Littenberg, Krumholz & Mentlik, LLP (57) ABSTRACT

An acetabular rim cutter has an annular cutting face provided on a rotatable carrier. A coupler is provided for attaching the carrier to a rotational power source. A guide element is axially aligned with the cutting face to locate and align the cutting face on the acetabulum with which it is to be used. Preferably, the guide element is axially movable in relation to the cutting face and a resilient element is provided for biasing it axially away therefrom.

8 Claims, 8 Drawing Sheets

U.S. PATENT DOCUMENTS

2003/0163135 A1* 8/2003 Hathaway .................... 606/80
2004/0073224 A1* 4/2004 Bauer ......................... 606/81
2004/0073226 A1* 4/2004 Cotting et al. ................ 606/91
2005/0159751 A1* 7/2005 Berthusen et al. ............. 606/80

FOREIGN PATENT DOCUMENTS

| | | |
|---|---|---|
| DE | 28 38 348 | 3/1980 |
| EP | 0 139 356 | 5/1985 |
| EP | 0 650 707 | 5/1995 |

* cited by examiner

ACETABULAR RIM CUTTER

BACKGROUND OF THE INVENTION

This invention relates to an acetabular rim cutter which can be used for cutting the outer rim of an acetabulum to form an annular seating surface to receive a flanged acetabular cup or a rim cutter and acetabulum reamer which has the dual function of reaming an acetabulum and then cutting its rim. Such a flanged cup is sold by Stryker Corporation as the Exeter™ Contemporary Flanged Cup.

Rotary cutters are known but use of such rotary cutters for treating the rim of an acetabulum is difficult because the surgeon has difficulty in locating the cutter with sufficient accuracy.

There are also difficulties in cutting the rim of an acetabulum so that the annular seating surface is a predetermined distance from the base of the acetabulum and that the part-spherical bearing surface of the cup is at a desired depth from the cut seating surface so that there is a regular seating surface. The present invention is intended to overcome some of the difficulties referred to above.

SUMMARY OF THE INVENTION

According to one aspect of the present invention an acetabular rim cutter comprises an annular cutting face provided on a rotatable carrier. A coupler is provided for attaching the carrier to a rotation power source. A guide element is axially aligned with the cutting face to locate and align the cutting face on the acetabulum with which it is to be used.

Preferably the guide element is axially movable in relation to the cutting face, and a resilient element is provided for biasing it axially away therefrom.

Thus, the guide element can be of a part-spherical shape which locates in the acetabulum and ensures that the axis of the annular cutting face is correctly aligned.

In a preferred embodiment the guide element is freely rotatable in relation to the rotatable carrier and it can be made from, for example, a synthetic plastics material.

The annular cutting face is preferably provided with radial cutting teeth.

An operating handle can be provided which is axially aligned in relation to the rotatable carrier and which is free to rotate in relation thereto thus providing a method for the surgeon to operate the equipment.

The rotatable carrier can be connected to an extension the end of which is adapted to receive the rotation source and on which the operating handle is located.

A depth cutting control system is also preferably provided which act to determine the depth and cut in relation to the base of the acetabulum with which it is to be used.

In order to provide a modular construction a number of guide elements can be provided which are used respectively to provide different depths of cut and which can be of different diameters to appropriately suit the acetabulum which is to be cut.

The apparatus can also include an acetabulum surface reamer which is adapted for attachment to the rotation means in place of the rotatable carrier and the guide element.

These aspects of the invention are provided by an acetabular cutter for preparing an acetabulum which has a hollow handle, a drive shaft rotatably mounted within the hollow handle with the shaft having a rotating head at a first end and a second end coupled to a power source. The power source may be an electrical or pneumatic powered hand piece. An acetabular rim cutter is connected to the drive shaft rotating head at a first end of the head with the cutting having teeth thereon concentric about a rotational axis of the head a preferably lying in a plane such as to be able to cut a circular groove around the rim of the acetabulum. A guide element is mounted on the handle for engaging the acetabulum and extending beyond the first drive shaft end. The guide element is axially movable with respect to the shaft of the drive axis and is spring-biased against the acetabulum so that the guide element may be placed within the acetabular cavity and the rim cutting element moved axially with respect hereto. The guide element is preferably dome shaped. Both the dome element and the rim cutter may be removably connected to the rotating head of the drive shaft so that cutters and elements of different sizes can be utilized. These cutter elements and drive tools may be supplied in a kit which includes one or more rotary drive tools, a plurality of dome shaped cutting elements which are used for preparing the acetabulum and a plurality of rim cutting elements to cut a groove around the cavity prepared by the dome shaped cutting elements. A plurality of rotary drive tool handles can be used of different lengths and even of different configurations such as being S-shaped or curved. A plurality of dome shaped members may also be provided.

BRIEF DESCRIPTION OF THE DRAWINGS

The invention can be performed in various ways but one embodiment will now be described by way of example and with reference to the accompanying drawings in which.

DETAILED DESCRIPTION

Figure 4:
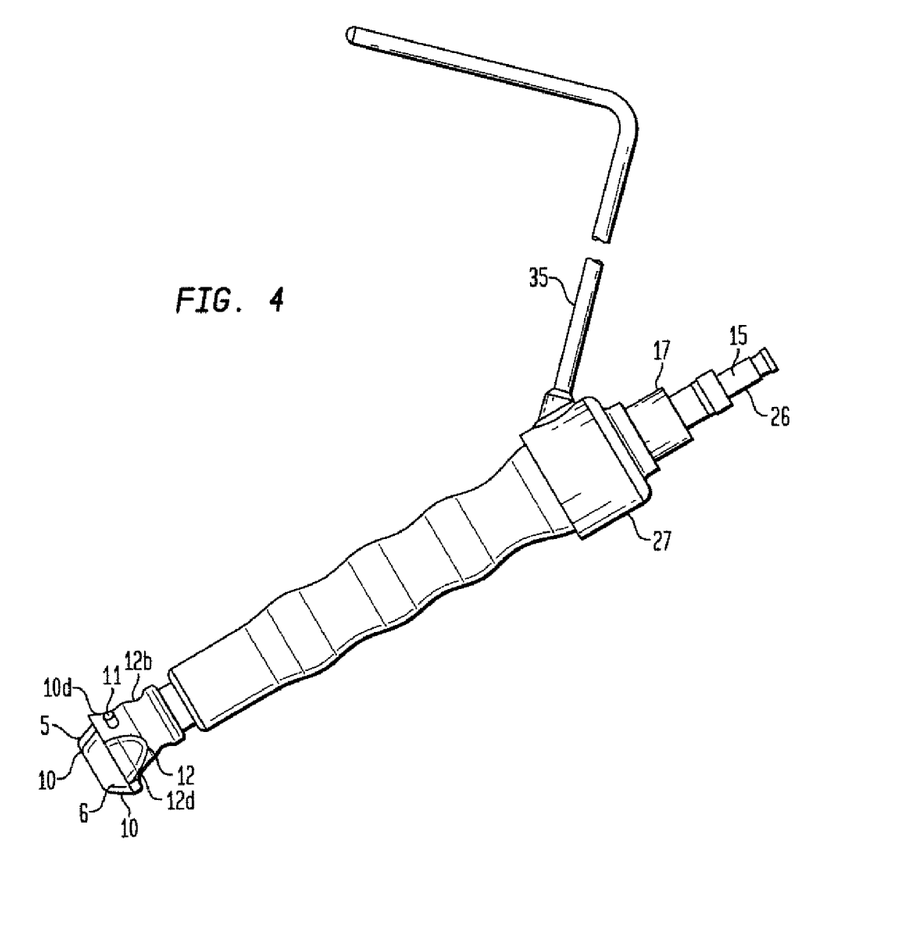
FIG. 4 is a side view of the rim cutter with the rotatable carrier removed.
Figure 5:
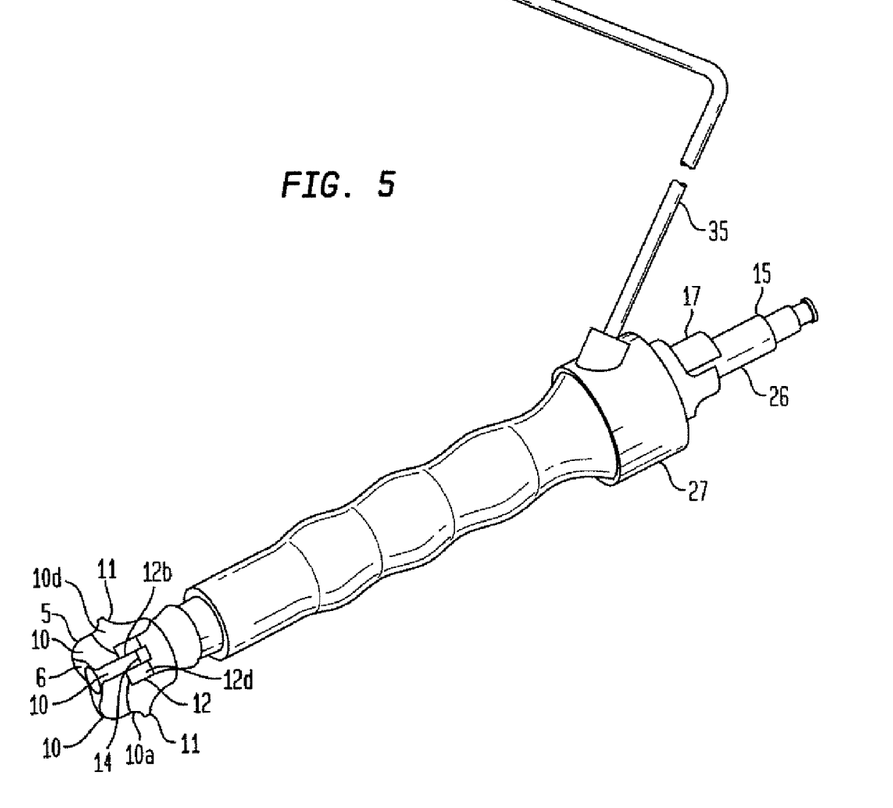
FIG. 5 is an isometric view of the rim cutter with the rotatable carrier removed.
Figure 6:
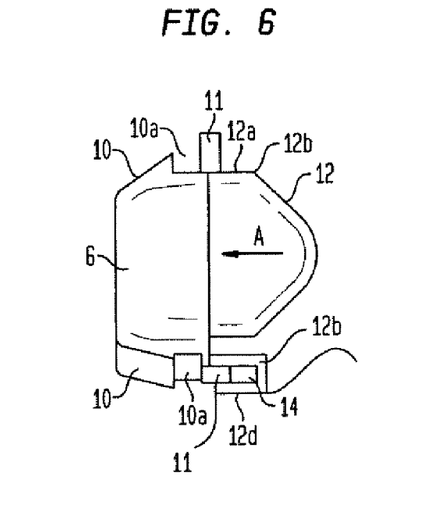
FIG. 6 is an enlarged side view of part of a first end of the rim cutter with the rotatable carrier removed.
Figure 7:
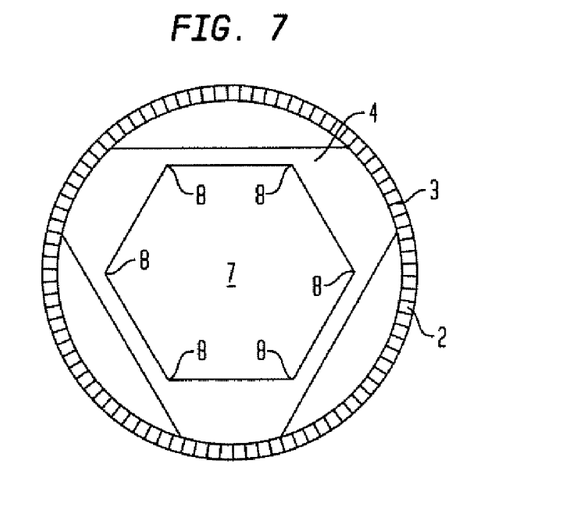
FIG. 7 is an end view of the rotatable carrier showing the annular cutting face.

As shown in the drawings an acetabular rim cutter according to a preferred embodiment of the present invention comprises an annular cutting face 2 which has radial cutting teeth 3 and which is provided on a rotatable carrier 4, the construction of which is most clearly shown in FIG. 6. The carrier 4 is attached to a hollow drive spindle 5 which has a triangular shaped end piece 6, most clearly shown in FIGS. 4, 5 and 6.

The carrier 4 has a hexagonal shaped opening 7 with corners 8 and which is dimensioned so that the distance of the wall between a first corner 8 and the next but one corner 8 circumferentially spaced around the hexagon is slightly greater than the length of the sides of the triangular end piece 6 between its corners 10 which are chamfered to accommodate the corners 8 of the hexagon. As best seen in FIG. 6 each corner 10 has a re-entry slot 10a one wall of which is provided by a corner 10 and the other of which is a projecting lug 11. The width of the slot 10a is adapted to receive and locate the wall of the carrier between two of the corners 8. Thus the carrier 4 can be passed over the triangular end piece 6 and then angularly rotated so that each of the corners 10 of the triangular end piece are aligned with one of the sides of the hexagon 7 between two of the corners 8. Movement in axial directions is prevented by the walls of the slot 10a.

Extending over the spindle 5 is a locking sleeve 12 which is biased towards the carrier by a spring 13 and the end of which is of similar shape to the triangular shaped end piece 6 but its corners 12a have flats 12b which are dimensioned to engage three of the sides of the hexagon 7 of the carrier 4. The corners 12 also have slats 14 which can engage the abutment 11. In FIG. 6 the sleeve is in its withdrawn position adjacent the spring bias and ready to receive the carrier 4. With the carrier in position the spring 13 will push the sleeve in the direction of the arrow A so that the flats 12b will engage the carrier so that it will rotate with the sleeve 12.

Located on the hollow drive spindle 5 is an extension shaft 15 on which is a freely rotatable operating handle 16 which has a pair of arcuate prongs 17, the inner diameters of which are less than the diameter of the extension shaft 15, and which engage a portion 26 of the shaft 15 which is of reduced diameter. The end of the handle and the prongs 17 are held in position by the resilient effect. The prongs 17 are also held by a retainer 27

Figure 1:
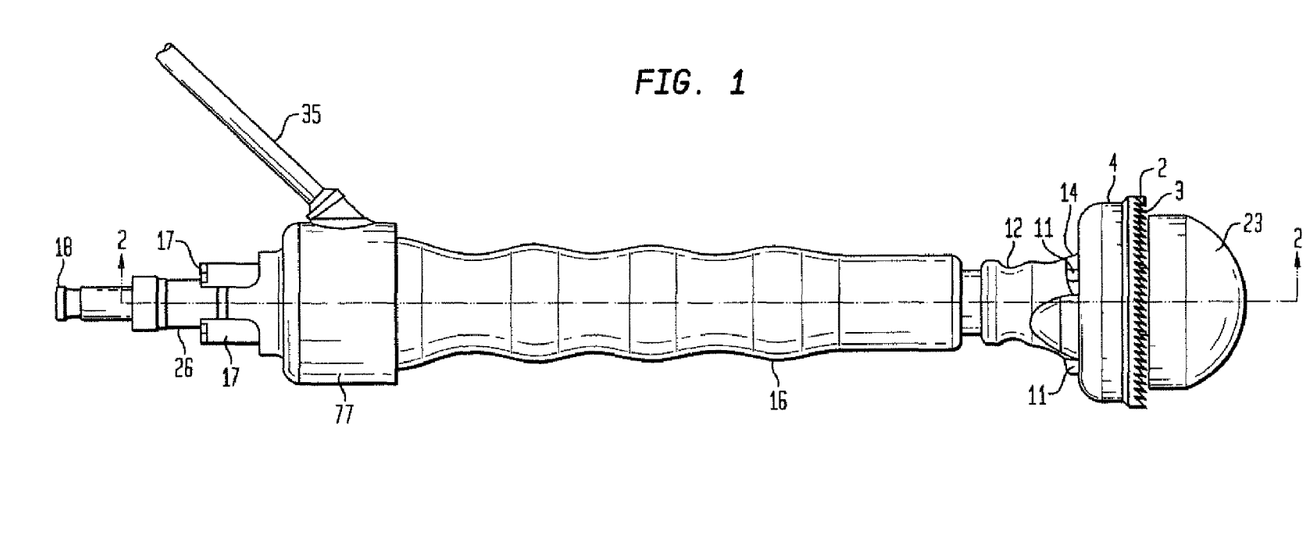
FIG. 1 is a side elevation of an acetabular rim cutter according to the present invention.
Figure 2:
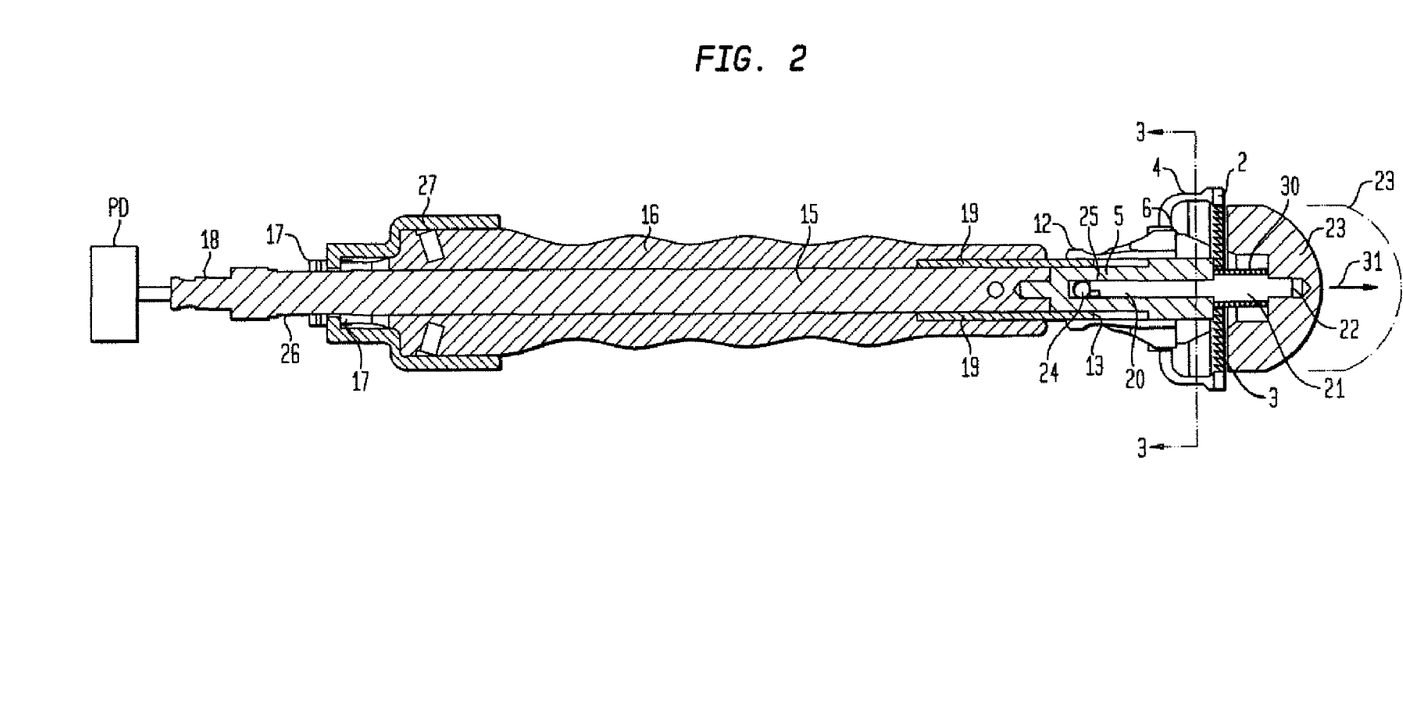
FIG. 2 is a cross-sectional view on the lines 2-2 of FIG. 1.

The outer end of the extension shaft 15 carries a boss 18 for connecting it to a rotary power drive of known type and which is indicated by reference letters PD in FIG. 2.

Also mounted on the extension shaft 15 is a sleeve 19 which extends into the locking sleeve 12 and retains the spring 13.

Figure 3:
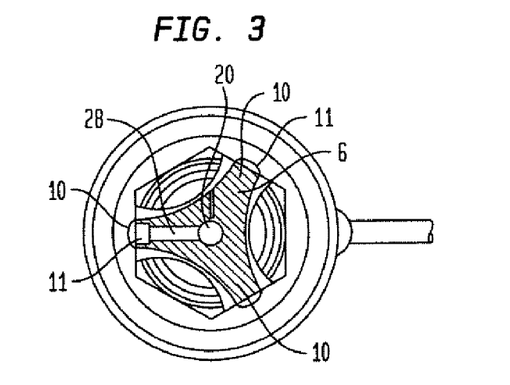
FIG. 3 is a cross-sectional end view on the line 3-3 of FIG. 2.

The hollow drive spindle 5 has a bore 20 in which is mounted a location shaft 21 the outer end 22 of which is screw threaded for attachment to a guide element 23 which has a part-spherical shape. The inner end 24 of the bore 20 has a location groove 25 which can be engaged by a resiliently biased plunger 28 which is carried in the triangular end piece 6 (as shown in FIG. 3).

Figure 2A:
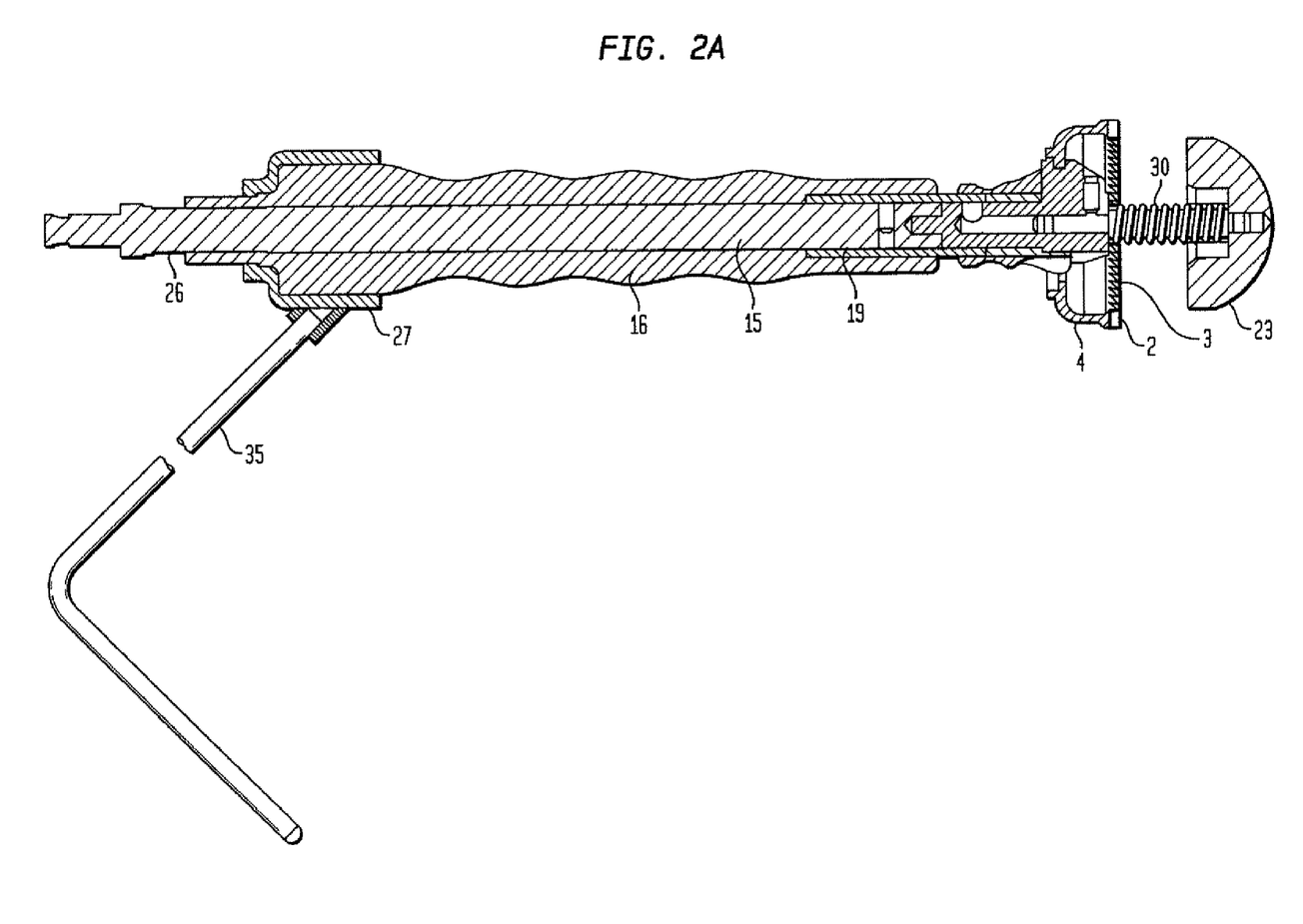
FIG. 2A is a cross-sectional view of FIG. 1 with the rim cutter spaced from the guide element.

The shaft 21 is biased to the right, as shown in FIG. 2, by means of a compression spring 30 mounted between the part-spherical guide element 23 and the hollow drive spindle 5. In FIGS. 2 and 2A the compression spring 30 is shown in a compressed position with the inner end 24 of the shaft 21 pushed into the full length of the bore 20. With the compression spring 30 in its expanded position the guide element 23 is pushed out to the position shown in chain lines on FIG. 2 in the direction of the arrow 31.

Figure 8:
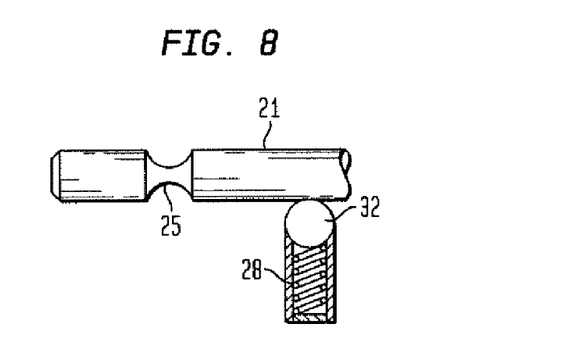
FIG. 8 is an enlarged diagrammatic side elevation of locking apparatus for determining the depth of cut.
Figure 9:
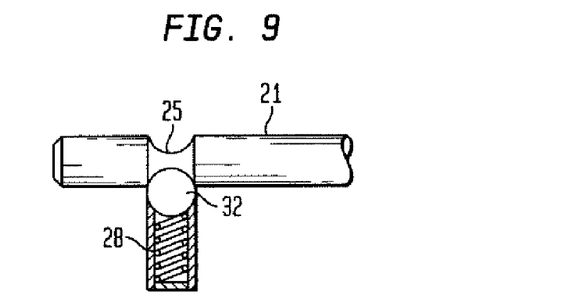
FIG. 9 is a view similar to FIG. 7 with the parts in a second position.

FIGS. 8 and 9 show how the spring loaded plunger 28 operates. The plunger has an engagement ball 32 which is pressed against the location shaft 21. The shaft 21 is first pushed into the bore 20 until the groove 25 is engaged by the plunger ball 32 which acts to hold it in position. The guide element is thus held in the position shown in chain lines in FIG. 2. When pressure is applied via the handle 16 and with the guide element in the acetabulum the shaft 21 moves up the bore and the ball 32 merely presses against the side of the shaft. The movement of the bore is against the pressure of the spring 30.

In an alternative construction (not shown) the spring loaded plunger 28 can be replaced by a resilient O-ring which can engage the groove 25 and can be mounted on the bore 20.

A location guide 35 of known kind is provided on the handle 16.

Figure 10:
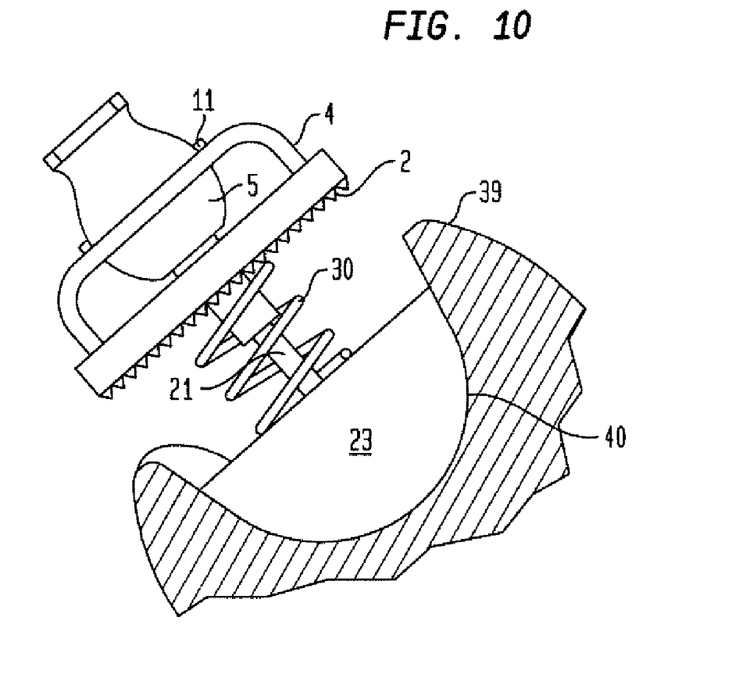
FIG. 10 is a partial side view showing the apparatus ready for use.
Figure 11:
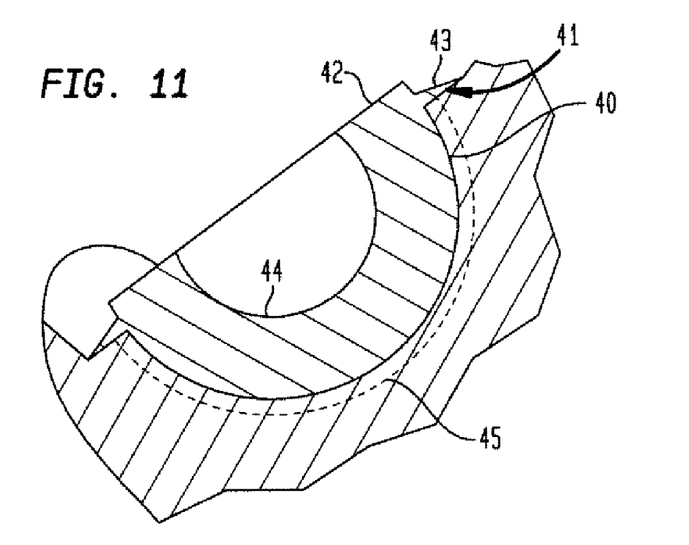
FIG. 11 shows a prosthetic acetabular cup in place in a reamed acetabulum.

FIGS. 10 and 11 show how the acetabular rim cutter, according to the present invention, can be used. The intention is to trim the outer edges 39 of an acetabulum 40 by machining an annular seating surface 41 as shown in FIG. 11. A flanged acetabular cup having an outwardly projecting flange 43 can now be seated on the annular seating surface 41. In the arrangement shown the cup is a close fit in the acetabulum but it will be appreciated that if, for example, the cup was to be held by cement then there could be an appropriate gap and spacers between the cup and the bone, as shown by chain lines 45.

FIG. 10 shows the operative end of the acetabular rim cutter according to the present invention and the same reference numerals are used to indicate similar parts to those shown in the other FIGS. The guide element 23 carried on the shaft 21 is in its extended position as caused by the spring 30 being expanded and it will be seen that the guide element 23 is axially aligned with the annular cutting face 2 by the rotatable head or carrier 4, although the guide element 23 is free to rotate in relation to the carrier 4. With power applied through the shaft 15 the carrier is rotated and is guided by the guide element 23 to the appropriate position to cut the annular bearing surface 41. The precise angles of cut can be determined in known manner using the guide 35.

The depth of cut of the annular bearing surface 41 is determined by the length of the shaft 21 which can be arranged so that the depth of the cut in relation to the base of the acetabulum 44 can be previously determined according to the length of the shaft 21. Thus, the surgeon can be provided with a series of cups of different shapes and shaft lengths to provide a modular construction which can be used in different circumstances depending upon the requirements of the type of acetabular cup used and the surgical implications.

The length of the shaft 21 therefore acts as depth cutting control means.

The guide element 23 can be made of any suitable material, for example metallic material.

Figure 12:
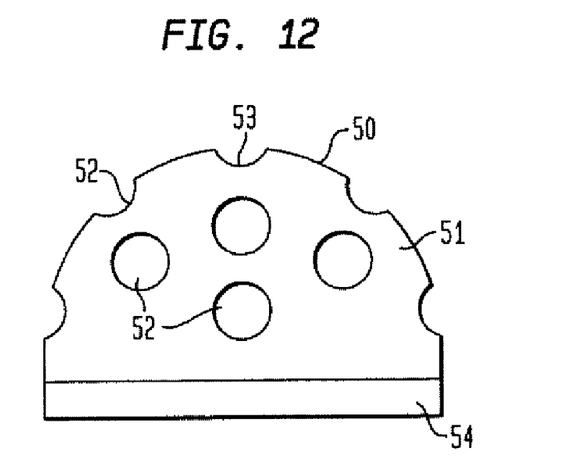
FIG. 12 is a side view of an acetabulum reamer which can be attached to the rotation system in place of the rotatable carrier; and, FIG. 13 is a bottom plan view of the acetabulum reamer shown in FIG. 11.
Figure 13:
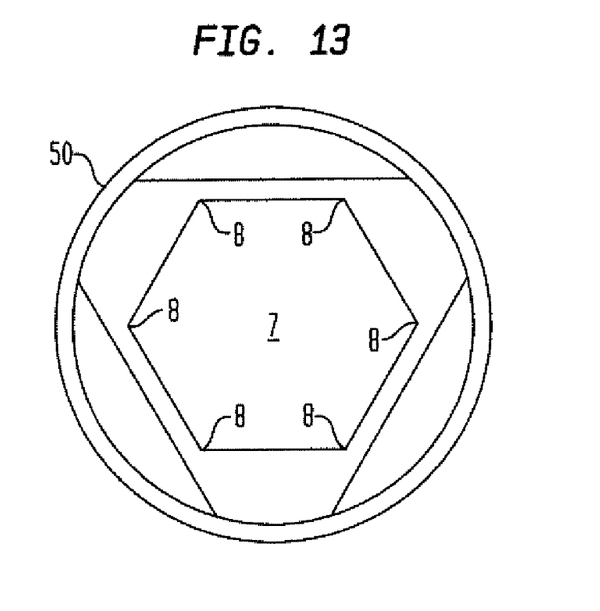

FIGS. 12 and 13 show an acetabulum reamer which can be used with the acetabulum rim cutter. The reamer 50 has a dome shaped portion 51, the outer surface of which is substantially part-hemispherical, and which is provided with a number of openings 52 which can be of any suitable shape but are shown as circular. These openings are provided with sharp corners 53 so that they will have a reaming effect when the reamer is placed in an acetabulum and rotated. This type of reamer is sometimes referred to as being of a "cheese-grater type".

The reamer has a base 54, the plan shape of which is best shown in FIG. 13. It will be seen that the shape is similar to the shape of the carrier 4 although it does not have the teeth 3. The same reference numerals are used to indicate similar parts to the carrier 4, thus, it has a hexagonal shaped opening 7 with corners 8, the dimensions are the same as those of the carrier.

The reamer can therefore be used with the rim cutter by removing the rotatable carrier 4 and replacing it with the reamer 50 thus enabling the apparatus to have a dual purpose.

The reamer can be attached first and used to ream the acetabulum with which it is to be used, the reamer can then be removed and replaced by the rim cutter.

The acetabular rim cutter or rim cutter and acetabulum reamer combined may particularly, although not exclusively, adapted for use with apparatus as set for in U.S. Pat. Nos. 5,879,402 and 6,264,698 for implanting an acetabular cup utilizing a loading tube.

The surgical technique on an exposed acetabulum cup will now be described.

The true medial wall of the acetabulum is identified by using reamers or a long-handled gouge to remove any curtain ostephytes and expose the true medial wall of the acetabulum.

Powered reamers are then used, increasing in size in 2 mm increments to remove cartilage and subchondral bone. Care is taken not to thin the walls excessively. A note is made of the largest reamer used to clear the rim of the acetabulum. Often it is useful to revert to a smaller reamer to further expose trabecular bone; particular attention is paid to the rim of the acetabulum since it is important to achieve interdigitation of bone in this area.

A step drill is used to make multiple holes. The smaller part of the drill is used all around the rim of the socket, the larger part of the step makes multiple holes in the dome of the ilium, pubis and ischium. Care is taken not to perforate the walls. If this does occur then morcellised bone graft is packaged into the hole to prevent egress of cement during cementation.

A cup with an outside diameter 2 mm smaller than the largest reamer used is usually the appropriate implant. The rim cutter marked with the same size as the cup is attached to a power tool. This will cut a groove in the periphery of the acetabulum of the appropriate diameter for the flange. The hemispherical guide of the rim cutter centralizes the cutter in the reamed socket and sets the depth of the rim and thus the position of the cup. The orientation of the rim cutter is shown by the alignment rod on the device. Alternately, the orientation may be accomplished by a computer-aided optical navigation system (see U.S. Pub. No. 2004/0153080. Accurate inclination and flexion can be ensured by using a navigation device on the shaft of the rim cutter. The rim cutter is advanced to the fullest extent allowed by exerting pressure against the spring between the dome and the cutting ring. Any debris created including the innermost fibers of the transverse ligament are excised. The flange is trimmed to the diameter defined by the chart to fit within the rim. A trial reduction may be carried out if desired.

An aspirator device is turned on at this point and, to save time, the nursing staff asked to start mixing the cement during final preparation of the bone. Thorough lavage of the socket is carried out to clean the interstices of the trabecular bone of marrow and fat. Fluid is aspirated out of the wing of the ilium by the aspirator. When the bone is clean, hydrogen peroxide soaked gauze swabs are packed into the socket to further clean the bone and promote haemostasis.

The cement may be handled approximately 3.5 minutes after mixing (Simplex™ P cement at 20 degrees centigrade). Immediately before the cement is placed in the socket, bone graft reamings may be impacted against the smooth cortical medial wall since the cement cannot adequately gain fixation against a surface of this sort. After introduction of the cement bolus excess material is removed so the surface of the cement lies with a slightly concave surface within the mouth of the socket. This step prevents the escape of surplus cement into the soft tissues when the acetabular pressurizer is applied.

The cement pressurizer consists of a saline filled balloon which can be inflated from a reservoir in the handle of the device. The pressurizing technique entails inflating the balloon so that it conforms perfectly with the mouth of the socket. Full body weight is applied to the device to drive the cement into the bone and, by maintaining pressure, protect the bone cement interface from back-bleeding from the host bone. The aspirator also serves to suck cement into the wing of the ilium and remove blood from the interface. If there is excessive blood loss through the aspirator the level of vacuum should be reduced.

The pressurizer is applied as soon as the cement has been placed in the socket and full pressure is maintained until the cement viscosity has risen to a level of viscosity suitable for the insertion in the cup—usually about 6 minutes after the commencement of mixing. In the elderly, or where it has been possible to expose a larger surface area of trabecular bone, it is possible that so much cement is pressurized into the acetabulum that a further bolus is required on top of the initial bolus of cement. This will become apparent when the pressurizer is removed. If more cement is to be used, then the existing cement should be dried before it is applied.

A flanged prosthetic cup is then inserted, as trialed, using an introducer and an axial pusher to drive the cup to the seated position. This insertion will likely require significant force and there should be a constant flow of cement around the edge of the cup. Excess cement can be removed with a small curette. The timing is perfect when the cup flange is delivered to the final seated position just as it is impossible to further advance the cup into the viscous cement. The post-operative radiograph should show good cement penetration and no radiolucent lines in any zone. The principle is to cut a rim around the periphery of the acetabulum to a set depth. The flange of the socket seats into this rim thus guaranteeing the correct orientation and depth of insertion of the socket if the rim cutter has been used correctly. Accurate positioning can be ensured since the rim cuter can be navigated to the desired position. Another benefit of this technique is that it allows the possibility of carrying out a trial reduction to test stability and leg length before cementation; the trimmed socket may be introduced into the acetabulum supported only by the flange resting in the rim and the hip reduced with the trial femoral component in place.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An acetabular cutter for preparing an acetabulum comprising:
   a hollow handle;
   a drive shaft extending along an axis rotatably and slidably mounted within said hollow handle, said shaft having a rotating head at a first end and a second end connected to a power source;
   an acetabular rim cutter connected to said drive shaft rotating head for axial and rotational movement thereof at the first end thereof, said cutter having teeth thereon concentric about a rotational axis of said head and the teeth, upon rotation, forms a planar annular cutting face extending in a plane perpendicular to the drive shaft axis capable of forming an outwardly facing annular planar surface around the circumference of the acetabulum in a plane perpendicular to the drive shaft axis;
   a guide element mounted on said handle freely rotatable with respect to the drive shaft for engaging the acetabulum and extending beyond said first drive shaft end, the guide element being axially movable along said rotational axis, the acetabular rim cutter movable with respect to the guide element in the direction of the axis of the drive shaft and having a diameter greater than a maximum diameter of the guide element; and a spring element acting between the guide element and the acetabular rim cutter along in the direction of the axis between the handle and the guide element and a stop means for limiting the travel of the rim cutter along the axis with respect to the guide element.

2. The acetabular rim cutter as set forth in claim 1 wherein the guide element is dome shaped.

3. The acetabular rim cutter as set forth in claim 2 wherein said guide element is capable of being biased into engagement with the acetabulum.

4. The acetabular rim cutter of claim 1 wherein said acetabular rim cutter is removably connected to said head.

5. A kit for preparing an acetabulum comprising:

a rotary drive tool having a hollow handle with a rotatable axially extending drive shaft therein, the drive shaft having a drive head at a first end and a connection for a power source at a second end;

a plurality of dome shaped cutting elements for preparing the acetabulum mountable on said drive head;

a plurality of rim cutting elements mountable on said drive head for rotational and axial movement therewith and having cutting teeth located along a circumference concentric about a rotational axis of said drive head, said teeth, upon rotation, forms an annular planar cutting face extending in a plane perpendicular to the rotational axis of the drive head capable of forming an outwardly facing annular planar surface around the circumference of the acetabulum in a plane perpendicular to the drive shaft axis; and a plurality of guide elements for mounting on the handle freely rotatable with respect to the drive shaft and a spring element for acting between the rim cutter and the guide element, the acetabular rim cutter movable with respect to the guide element in the direction of the axis of the drive shaft and having a diameter greater than a diameter of the guide element, each guide element including a stop means for limiting the movement of a rim cutter with respect to the guide element in the axial direction of the drive shaft.

6. The kit as set forth in claim 5 further comprising a plurality of dome shaped guide elements mountable on said handle.

7. The kit as set forth in claim 6 wherein said guide element is capable of being biased into engagement with the acetabulum.

8. The acetabular rim cutter as set forth in claim 5 further comprising a plurality of handles of different lengths.

* * * * *